United States Patent
Kelsen

(10) Patent No.: US 10,058,627 B2
(45) Date of Patent: Aug. 28, 2018

(54) DIGITAL AROMA CASSETTE CARTRIDGE AND MATRIX DISPERSION SYSTEM FOR REMOTE CONTROLS

(71) Applicant: 5TH SCREEN DIGITAL INC., Scotts Valley, CA (US)

(72) Inventor: Keith Kelsen, Scotts Valley, CA (US)

(73) Assignee: Inhalio, Inc., Scotts Valley, CA (US)

( * ) Notice: Subject to any disclaimer, the term of this patent is extended or adjusted under 35 U.S.C. 154(b) by 108 days.

(21) Appl. No.: 15/501,818

(22) PCT Filed: Jul. 25, 2016

(86) PCT No.: PCT/US2016/043926
§ 371 (c)(1),
(2) Date: Feb. 3, 2017

(87) PCT Pub. No.: WO2017/019630
PCT Pub. Date: Feb. 2, 2017

(65) Prior Publication Data
US 2017/0216474 A1    Aug. 3, 2017

Related U.S. Application Data

(60) Provisional application No. 62/196,299, filed on Jul. 24, 2015.

(51) Int. Cl.
| | | |
|---|---|---|
| *A61L 9/12* | (2006.01) | |
| *B01F 3/04* | (2006.01) | |
| *A01M 29/12* | (2011.01) | |
| *G06F 13/14* | (2006.01) | |
| *A63F 13/24* | (2014.01) | |
| *A63H 30/04* | (2006.01) | |
| *A63J 5/00* | (2006.01) | |

(Continued)

(52) U.S. Cl.
CPC ............ *A61L 9/122* (2013.01); *A01M 29/12* (2013.01); *A63F 13/24* (2014.09); *A63H 30/04* (2013.01); *A63J 5/00* (2013.01); *A63J 25/00* (2013.01); *B01F 3/04007* (2013.01); *B01F 3/04085* (2013.01); *G06F 13/14* (2013.01); *H04N 21/4131* (2013.01); *A61L 2209/111* (2013.01); *A61L 2209/133* (2013.01); *A61L 2209/134* (2013.01); *A61L 2209/15* (2013.01); *A63J 2005/008* (2013.01); *H04R 1/1008* (2013.01); *H04R 1/1058* (2013.01); *H04R 1/1091* (2013.01); *H04W 4/80* (2018.02)

(58) Field of Classification Search
CPC .... B01F 3/04; B01F 3/04085; B01F 3/04007; A61L 9/122; A61L 9/125
USPC ................. 261/30, DIG. 88; 422/124; 96/421
See application file for complete search history.

(56) References Cited

U.S. PATENT DOCUMENTS

| | | | | |
|---|---|---|---|---|
| 6,783,117 B2 * | 8/2004 | Wohrle | .................... | A61L 9/035 261/104 |
| 7,484,716 B2 * | 2/2009 | Ford Morie | ............. | A61K 8/02 239/58 |

* cited by examiner

*Primary Examiner* — Robert A Hopkins

(57) ABSTRACT

The present invention is directed to a digital aroma system that provides a scented air on demand to various devices in various forms and user held devices including: remote controls, video game controllers and mobile computing devices. Dry fragrance infused substrates are contained in fragrance cartridges that are removably mounted in a cassette that is connected to a manifold that has airway passages that are connected to fans or pumps that are controlled by a computer processor. In response to a fragrance control signal or a fragrance trigger, the processor can selectively direct scented air having a specified fragrance to a system user.

44 Claims, 19 Drawing Sheets

(51) Int. Cl.
*A63J 25/00* (2009.01)
*H04N 21/41* (2011.01)
*H04W 4/80* (2018.01)
*H04R 1/10* (2006.01)

DIGITAL AROMA CASSETTE CARTRIDGE AND MATRIX DISPERSION SYSTEM FOR REMOTE CONTROLS

CROSS REFERENCE TO RELATED APPLICATIONS

This patent application claims priority to U.S. Provisional Patent Application No. 61,196,299, "Digital Aroma Cassette Cartridge And Matrix Dispersion System For Remote Controls" filed Jul. 23, 2015 which is hereby incorporated by reference in its entirety.

FIELD OF INVENTION

This invention relates to a device and system for creating an aroma experience for users who interact with a remote control device and other devices.

BACKGROUND

Fragrance systems exist for commercial and home applications. In some embodiments, fragrance systems provide aromas, which can elicit various emotional feelings that can improve moods and increase feelings of happiness. Machines exist which distribute fragrances for commercial and home applications. For example, scented oils have been used to emit fragrances. However, many scented oils such as pine oil, lavender oil, geranium oil, etc. include monoterpenes which may be carcinogens. Some studies have shown the rats and mice that had scented oils injected into their throats resulted in kidney tumors. What is needed is an improved fragrance system, which does not use scented oils and is not carcinogenic.

SUMMARY OF THE INVENTION

The present invention is directed to a digital aroma system that provides aroma experiences that can be utilized in the market place, specifically gamming and watching television and movies. The present invention is a digital aroma system that utilizes dry fragrance infused beads or other solid substrate that contain porous fragrance materials contained in a fragrance cartridge(s) that is removable mounted in an interchangeable cassette system that that connects to a manifold. The manifold has specific airway passages that are connected to fans or pumps that are controlled by a computer processor. In response to a fragrance control signal or a fragrance trigger, the processor can selectively direct air into the any individual target fragrance cartridge. More specifically the processor can cause the fan or pump to pull or push fresh unscented air through the target fragrance cartridge and the fresh air passes by the particles infused with a dry fragrance material. The aroma reaches the individual through one or several outlets.

The invention digital aroma system is designed to fit into a very small footprint while providing many aromas that enhance the user experience of the game or movie. In an embodiment the digital aroma system can simultaneously hold numerous (for example six) distinct fragrance cartridges. The digital aroma system can be coupled to or integrated into a game controller or any other device that is used for control entertainment, such as a remote control or headset which may include a speaker for receiving audio signals and a microphone for transmitting sound commands. The digital aroma system can be configured in many different forms to match the entertainment remote control device including a handheld device.

The digital aroma system invention can include a processor that runs computer software that creates a visual, audio, and/or smell sensory experience. This computer processor of the digital aroma system can also communicate with remote computers in a cloud based system and/or a remote server. These remote computers can interact with the local digital aroma system software to provide live interactive experiences to the system users. In an embodiment, the digital aroma system can communicate wirelessly through Blue Tooth, Wi-Fi, RFID or similar technologies with other devices which can provide control signals or triggers for releasing fragrances.

The digital aroma system can include a processor that can control and monitor the operation of the system components. The processor can be coupled to fans and/or valves to selectively direct air to the target fragrance cartridge. When a desired fragrance signal or trigger is detected, the processor can direct fresh air through the air inlet to the target fragrance cartridge. The dry fragrance can mix with the fresh air and be directed to a scent outlet to the system user. In some embodiments, the processor can direct fresh air through two or more target fragrance cartridges to provide a mixed fragrance to the user. The scent is provided as a limited predetermined period of time or volume of air. Once the scent is provided to the user, the processor can the stop the flow of air through the fragrance cartridge by stopping a fan(s) or closing a valve(s). In an embodiment, the processor can be programmed to flush the scent outlet of the manifold periodically with fresh air so that subsequent fragrances are not mixed or contaminated. For example, the processor may direct fresh air through the scent outlet after each fragrance output by the system.

The digital aroma system can release fragrances based upon control signals or triggers. The digital aroma system can include a receiver, which receives fragrance signals. In response to the fragrance signals, the processor can identify the corresponding target fragrance cartridge and direct air to the target fragrance cartridge, which can result in the dry fragrance device delivering a dry fragrance aroma to the user. In other embodiments, the digital aroma system can respond to triggers such as images or sounds.

It also relates to a gaming device and any remote control device that delivers aroma to an individual. It relates to a system that is uniform in nature and has consistent form for replacement of aromas similar to a cartridge laser printer.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION

A detailed description of one or more embodiments of the invention is provided below along with accompanying figures that illustrate the principles of the invention. While the invention is described in conjunction with such embodiment(s), it should be understood that the invention is not limited to any one embodiment. On the contrary, the scope of the invention is limited only by the claims and the invention encompasses numerous alternatives, modifications, and equivalents. For the purpose of example, numerous specific details are set forth in the following description in order to provide a thorough understanding of the present invention. These details are provided for the purpose of example, and the present invention may be practiced according to the claims without some or all of these specific details. For the purpose of clarity, technical material that is known in the technical fields related to the invention has not been described in detail so that the present invention is not unnecessarily obscured.

Figure 1:
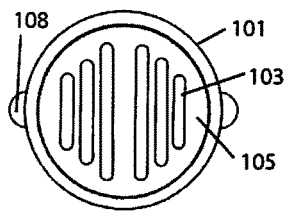
FIG. 1 illustrates a bottom view of an embodiment of a fragrance cartridge.
Figure 2:
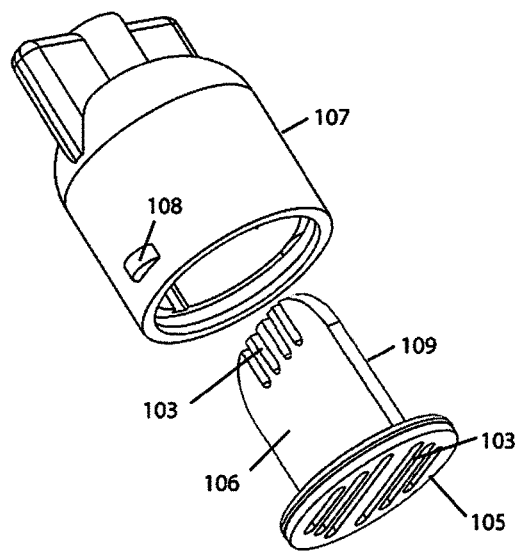
FIG. 2 illustrates a bottom perspective view of an embodiment of a fragrance cartridge.
Figure 3:
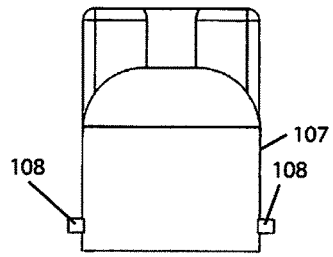
FIG. 3 illustrates a side view of an embodiment of a fragrance cartridge.
Figure 4:
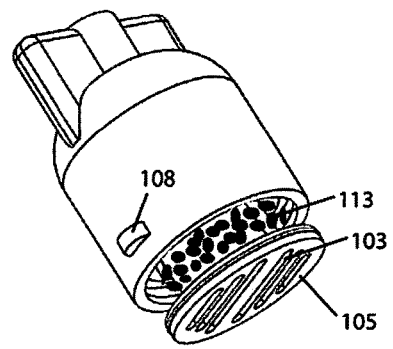
FIG. 4 illustrates a bottom perspective view of an embodiment of a fragrance cartridge.

An embodiment of a fragrance cartridge is illustrated in FIGS. 1-4. FIG. 1 illustrates a bottom view of an embodiment of the fragrance cartridge 101 with a plurality of air flow slots 103 in the bottom surface 105. FIG. 2 illustrates a perspective view of the fragrance cartridge 101 in a disassembled state. In this embodiment the fragrance cartridge 101 includes an upper housing 107 which has an internal volume and a lower housing 109 which has a lower surface 105 and a center divider 106 having air flow slots 103. FIG. 3 illustrates a side view of a fragrance cartridge 101 that has a two piece housing that includes an upper housing 107 and a lower housing 109 that are secured together to form the complete housing for the fragrance cartridge 101. FIG. 4 illustrates a perspective view of the fragrance cartridge 101 in a disassembled state. The upper housing 107 can be filled with a plurality of substrates 113 that are infused with a dry fragrance. In an embodiment the substrates 113 can be spherical balls or other three dimensional objects such as cubes, cylinders, particles or other geometric volumes. While the fragrance cartridge 101 is illustrated as a dome shape with slots 103 in the lower surface 105 and the lower surface 109, in other embodiments the fragrance cartridge can have any other geometric shape that can hold the plurality of substrates 113. When air flows through the cartridge 101, the dry fragrance can mix with the air and be removed from the substrates 113 resulting in scented air exiting the cartridge 101. In an embodiment, the fragrance cartridge 101 can have a cylindrical shape that can be placed into a corresponding cylindrical bore. In an embodiment tabs 108 can be mounted on the outer surface of the cartridge 101 which are used to secure the cartridge to a cassette.

Figure 5:
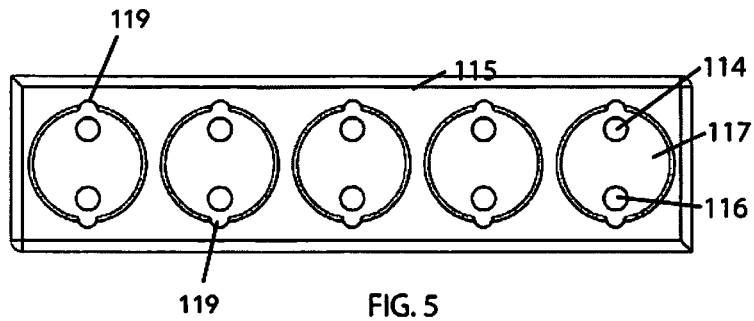
FIG. 5 illustrates a top view of an embodiment of a cassette that holds a plurality of fragrance cartridges.
Figure 6:
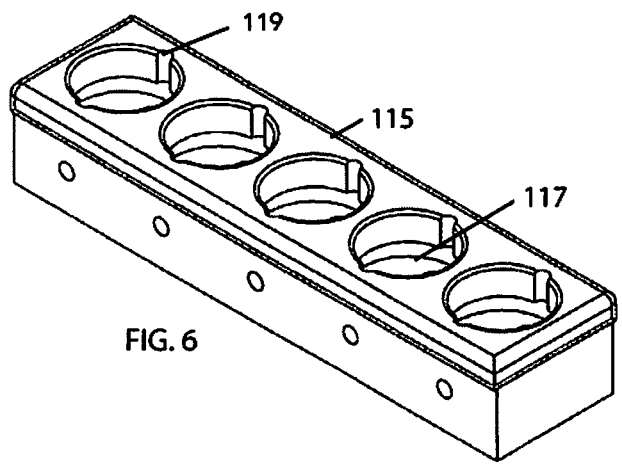
FIG. 6 illustrates a top perspective view of an embodiment of a cassette.
Figure 7:
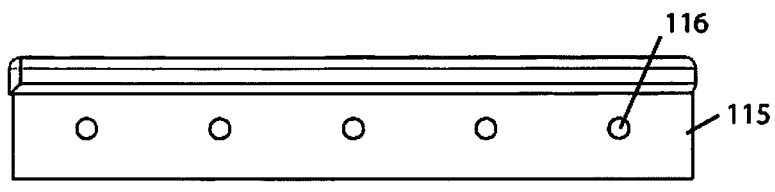
FIG. 7 illustrates a side view of an embodiment of a cassette.

In an embodiment with reference to FIGS. 5-8 an embodiment of a fragrance cassette matrix 115 is illustrated. FIG. 5 illustrates a top view of a fragrance cassette matrix 115 and FIG. 6 illustrates a perspective top view of the cassette matrix 115. The cassette matrix 115 can have cartridge openings 117 that each holds a fragrance cartridge. FIG. 7 illustrates a side view of the cassette matrix 115. The illustrated embodiment of the cassette matrix 115 can have five cartridge sockets 117 that securely hold five fragrance cartridges 101 in a single row configuration. The cartridge sockets 117 in the cassette matrix 115 can each have two air channels one inlet 114 and one outlet 116 and are keyed so that fragrance cartridges 101 can be easily placed in and removed from the sockets 117. The cartridge openings 117 can have tab slots 119 which can be aligned with the cartridge tabs and provide a mechanism for securing the fragrance cartridges to the cartridge sockets 117. For example, when the fragrance cartridge is placed in the cartridge socket 117, the cartridge tabs can be placed in the tab slots 119. Once the fragrance cartridge is fully inserted into the cartridge socket 117, the fragrance cartridge can be axially rotated within the socket 117 so that the tabs are no longer aligned with the tab slots 119. By offsetting the tabs from the tab slots 119, the fragrance cartridge can be secured within the cassette matrix 115.

Figure 8:
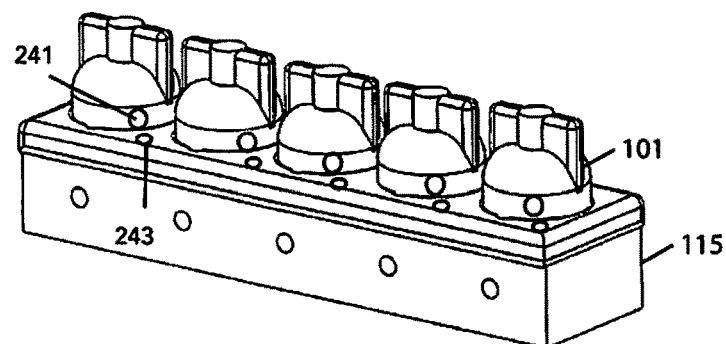
FIG. 8 illustrates a top perspective view of an embodiment of a cassette with a plurality of fragrance cartridges.
Figure 9:
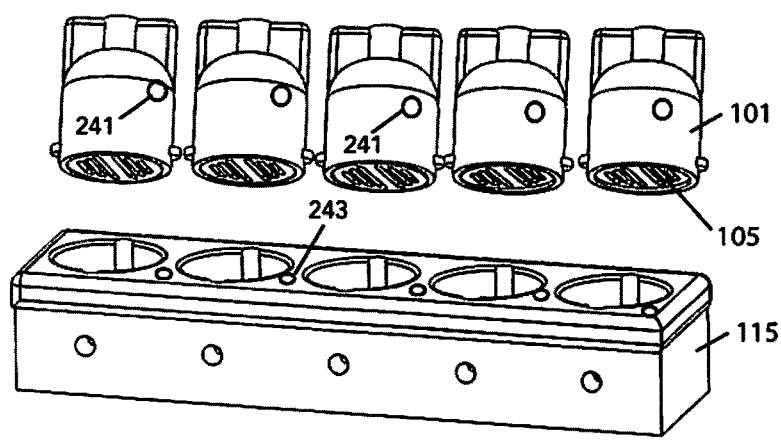
FIG. 9 illustrates a perspective view of an embodiment of a cassette with a plurality of fragrance cartridges.

FIG. 8 illustrates a perspective top view of the cassette matrix 115 with the fragrance cartridges 101 positioned in the cartridge sockets 117. In the illustrated embodiment, the cartridges 101 have been inserted into the cartridge sockets 117 with the tabs aligned with the tab slots and then rotated 90 degrees after being fully inserted. FIG. 9 illustrates a perspective view top view of the cassette matrix 115 and with the cartridges 101 positioned over the sockets openings. The cartridges 101 are interchangeable within the cassette matrix 115.

Figure 10:
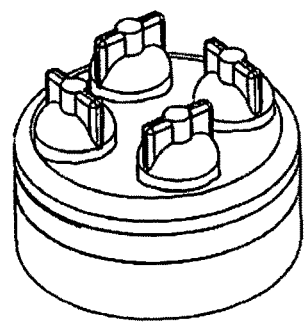
FIG. 10 illustrates a top perspective view of an embodiment of a cassette with a plurality of fragrance cartridges.

As discussed each cartridge 101 can include identification information which identifies the fragrance so that the digital aroma system can properly direct air to the target fragrance cartridge 101 regardless of its position in the cassette matrix. For example, in an embodiment, each fragrance cartridge 101 can include a radio frequency identification (RFID) tag 241 and the cassette matrix 115 can include RFID readers. The RFID tag 241 can transmit fragrance identification and a number of fragrance dispersions and a cartridge identification code. The RFID reader 243 can read the identification information from the RFID tag 241 on the fragrance cartridge 101 and additional cartridge information, which can be used by the system. For example, the system display the fragrance on a system output and direct the air to the proper fragrance cartridge 101. In other embodiments, the cassette matrix can hold more fragrance cartridges 101 in different configurations such as a 2×6, 3×8 or any other one or two ore three dimensional array configuration including circular cassette matrix 120 configuration as illustrated in FIG. 10.

Figure 11:
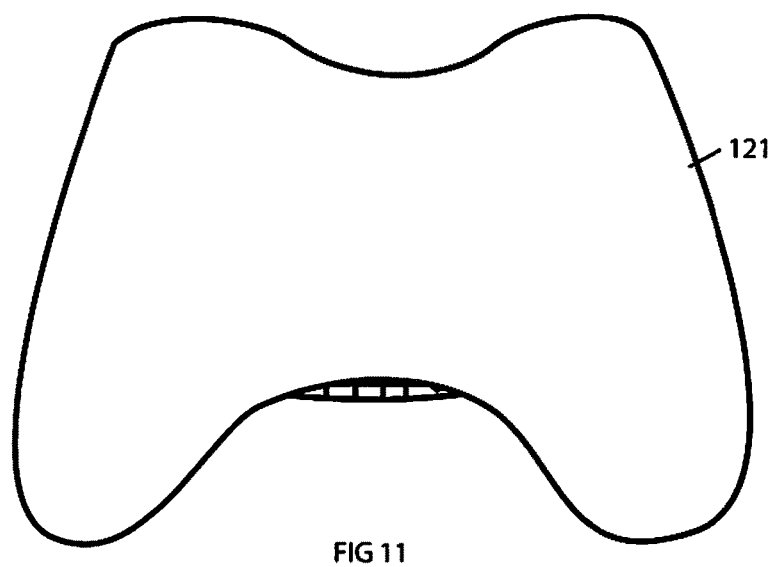
FIG. 11 illustrates a top view of an embodiment of a controller with a digital aroma system.
Figure 12:
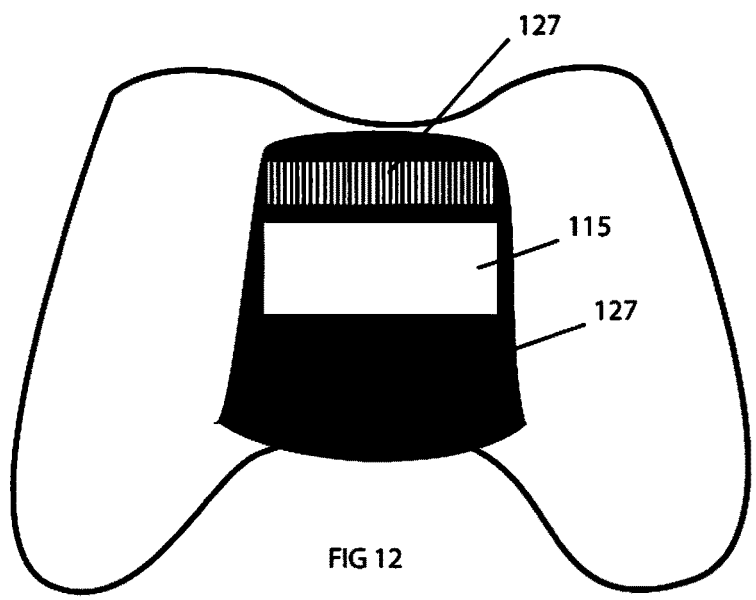
FIG. 12 illustrates a bottom view of an embodiment of a controller with a digital aroma system.

The cassette 115 with fragrance cartridges 101 can be used with various digital aroma system assemblies. FIG. 11 illustrates a top view of an embodiment of a video game controller 121 and FIG. 12 illustrates a bottom view of the video game controller 121 which can communicate with a video game player. A video game player can use the video game controller 121 as a user interface with a video game. In the illustrated embodiment the digital aroma system 123 is mounted on the bottom of the controller 121 since most motion control buttons and joysticks can be mounted on the upper surface. The digital aroma system 123 can include a cassette slot 127 for the cassette 115 that holds a plurality of fragrance cartridges. The digital aroma system 123 can include an air inlet that can draw air from the front of the controller 121 and an air outlet that can direct scented air from the rear of the controller 121 towards the user. The controller 121 can be coupled to a video game player which can provide triggers or signals for emitting fragrances to the digital aroma system 123 which can respond by emitting the corresponding designated fragrances which can be smelled by the user.

Figure 13:
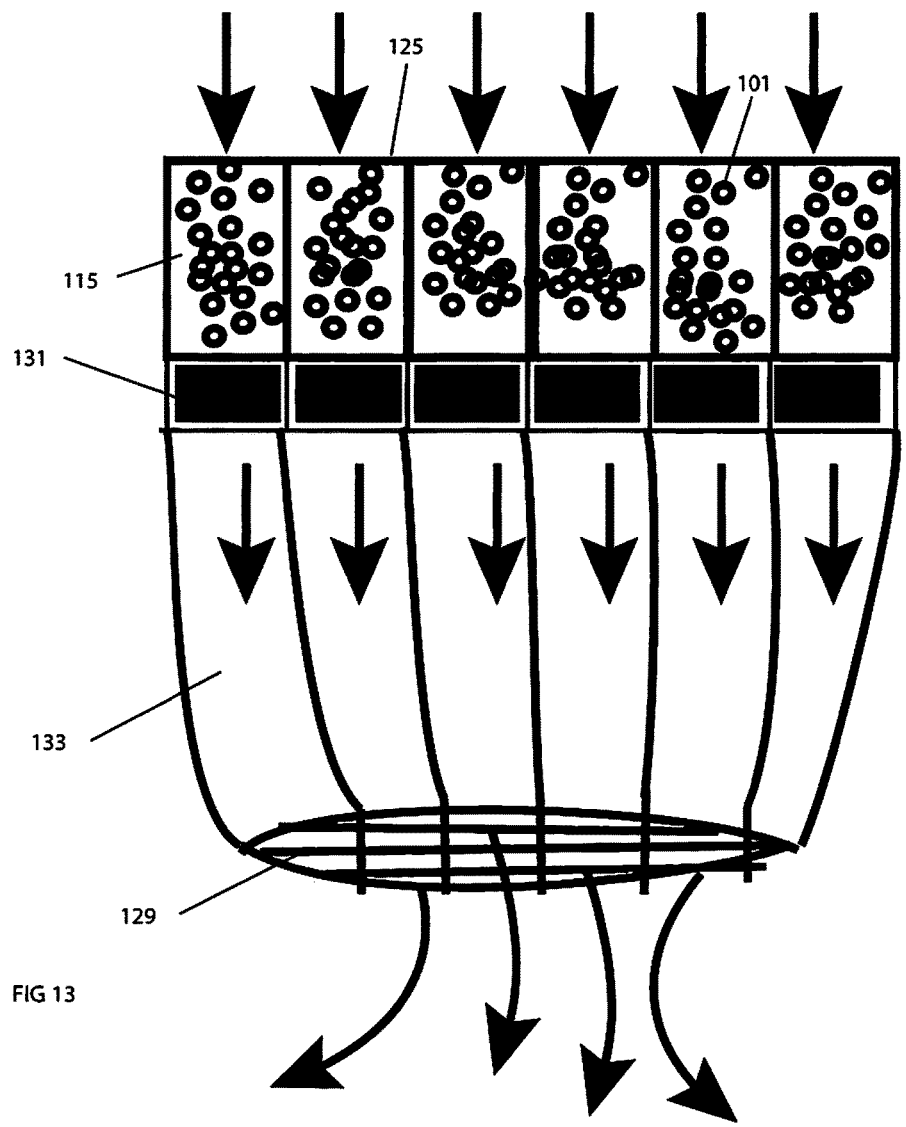
FIG. 13 illustrates the components of an embodiment of a digital aroma system.
Figure 14:
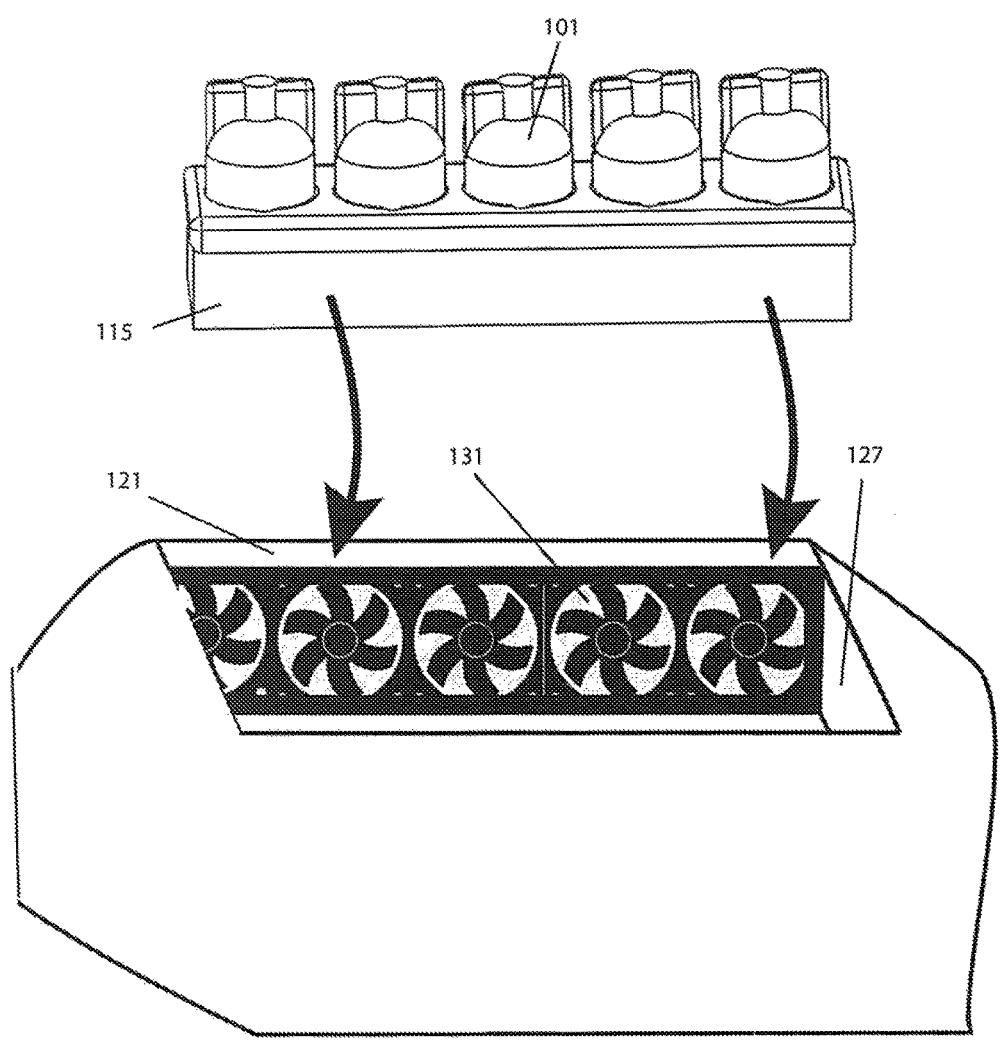
FIGS. 14 and 15 illustrate bottom views of different embodiments of controllers with the cassettes removed.

FIG. 13 illustrates an embodiment of the digital aroma system 123 used with remote controls that shows the airflow paths through the system components. The cassette 115 with the fragrance cartridges 101 can be mounted adjacent to the air inlet 125. The fragrance cartridges 101 can each be filled with substrates 113 which are infused with dry fragrances. Micro fans 131 that are individually controlled can be mounted in the digital aroma system 123 adjacent to the cassette 115. The micro fans 131 can be coupled to a processor that selectively actuates the micro fans 131 and directs scented air into a manifold 133 which can include a separate air flow path or channel for each fragrance cartridge 115. By having separate air flow paths for each fragrance cartridge in the manifold 133, there is no contamination and/or mixing of the different scents from the fragrance cartridges 101. The scented air exits the air outlet 129 and is directed towards the user holder of the controller 121. In this configuration, the micro fans 131 create a low gas pressure, which pulls air through the fragrance cartridges 101. In an embodiment, the micro fans 131 can be placed at the scented air outlet 129 so that the manifold 133 is between the cassette and micro fans 131. In other embodiments the micro fans can be positioned before the cassettes to create higher gas pressure that push air through the fragrance cartridges 101. Thus, the micro fans 131 can be placed in various different positions that creates an vacuum and sucks the air through the cartridges 101 and then pushes the air through the manifold. In different embodiments the fans 131 can be replaced by micro pumps FIG. 14 illustrates a back view of the bottom of an embodiment of the controller 121 with an integrated digital aroma system 123 that includes a cassette slot 127 and micro fans 131. To use the digital aroma system 123 the cassette 113 filled with fragrance cartridges 101 can be inserted into the cassette slot 127. The fans 131 are placed forward of the cassette 113 and the manifold. When the digital aroma system 123 is actuated to release a scent, one (or more) of the fans 131 is actuated that creates high pressure that pushes air through the cartridge 101 containing the designated fragrance. The air flow generated by the fans 131 blows scented air through the manifold towards the user of the controller 121.

Figure 15:
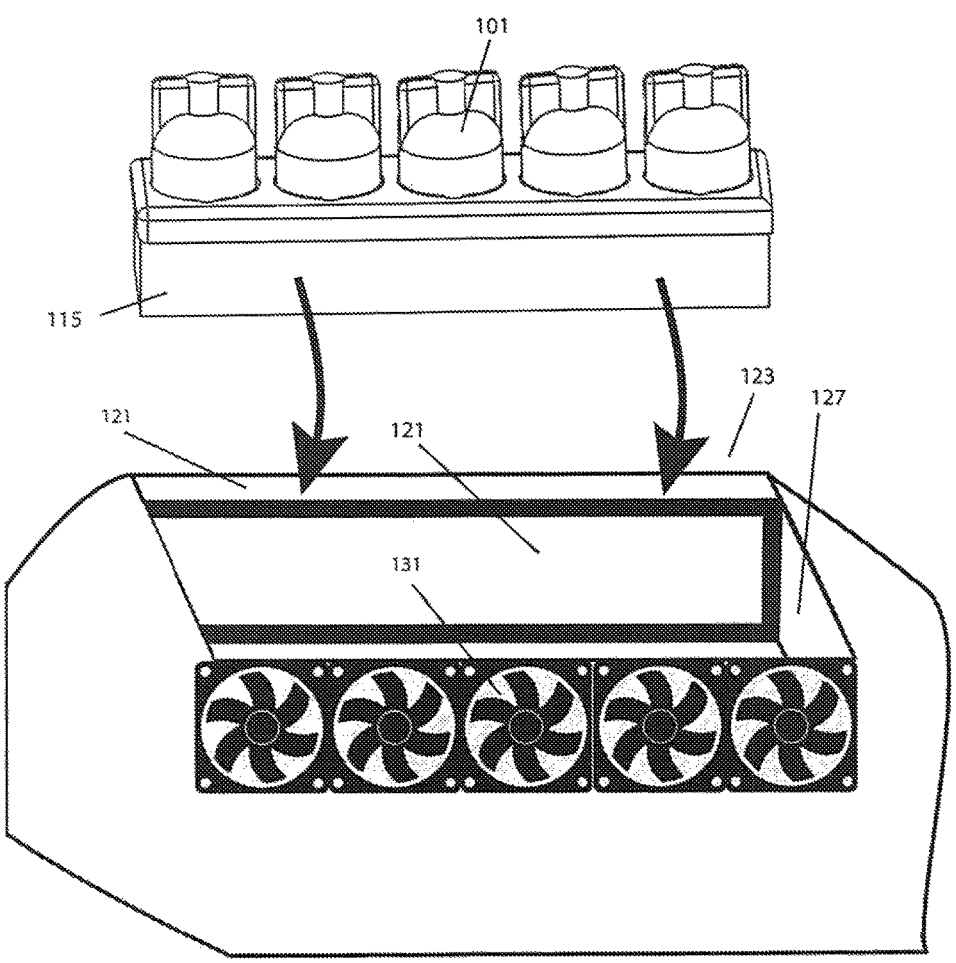

FIG. 15 illustrates a back view of the bottom of another embodiment of the controller 121. In this embodiment, the micro fans 131 are mounted in a down stream position relative to the cassette slot 127. In this configuration, the cassette slot 127 can be adjacent to the air inlet 125. When the digital aroma system 123 is actuated to release a scent, one of the fans 131 is actuated creating a vacuum that pulls air through the cartridge 101 containing the designated fragrance to blow scented air through the manifold towards the user of the controller 121.

Figure 16:
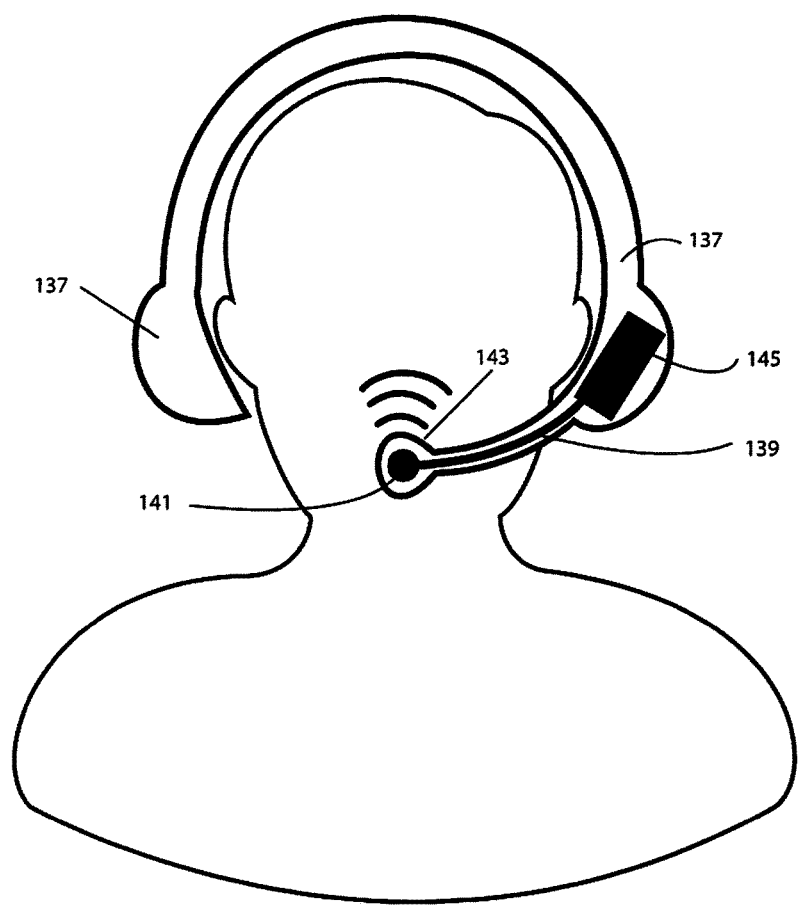
FIG. 16 illustrates an embodiment of a headset that includes an integrated digital aroma system.

FIG. 16 illustrates a headset 135 that includes an integrated digital aroma system 123. In this embodiment headset 135 that includes ear cups 137 which can include speakers that emit sound and a mouthpiece 143 that includes a microphone that is used for receiving voice commands. In the illustrated configuration, most of the digital aroma system 145 components including the cassette with replaceable fragrance cartridges, fans and check valves can be mounted in one of the ear cups 137. An air passageway 139 can be built into an arm, which extends from the ear cup 137 to the mouth. When the digital aroma system 145 is actuated to release a scent, one of the fans is actuated that directs air through the fragrance cartridge and blows the scented air through the air passageway towards the nose of the user wearing the headset 135.

Figure 17:
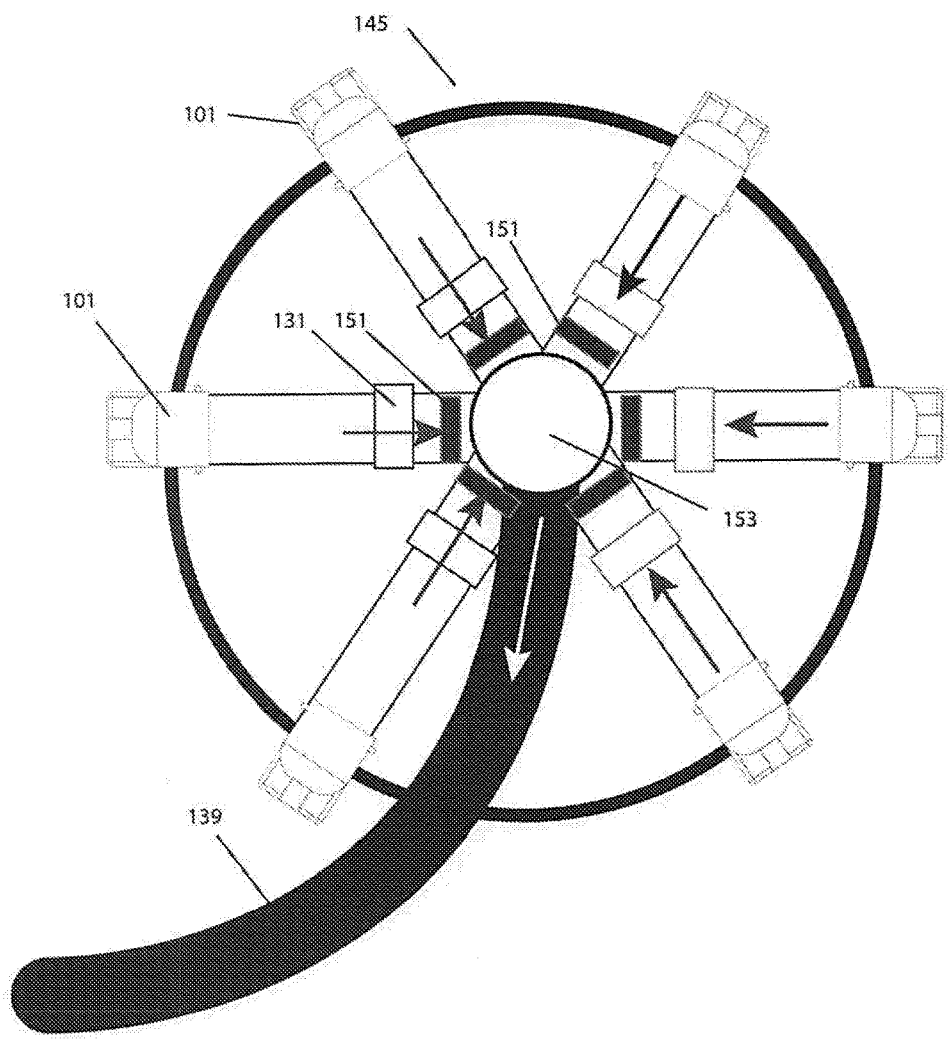
FIG. 17 illustrates an embodiment of digital aroma system components for a headset.

Details of the configuration of an embodiment of the digital aroma system 145 used with the headset system are shown in FIG. 17. In this embodiment, the digital aroma system 145 can include fragrance cartridges 101 which can be individually placed into cartridge holes 147 around the outer surface of the ear cups of the headset with the inlet sides of the cartridges 101 exposed to ambient air. Thus, in this embodiment the digital aroma system 145 may not include a cassette. The user can easily access and exchange each of the individual fragrance cartridges 101. Air passage ways 139 can connect each of the fragrance cartridges 101 to a corresponding fan 131 which can blow the scented air from the outer edge of the ear cup 137 into an inner circle 149 and then through an air passageway 139 to the nozzle outlet 141. When a fragrance is to be delivered to a user, a micro fan 131 is actuated which draws air into the interior volume 153 of an ear cup 137 of the headset 135. This air movement pulls fresh ambient air through the fragrance cartridge 101. The scented air is then directed through the air passageway 139 and out an outlet nozzle adjacent to the face of the headset wearer. Also located with the within the passageways of the digital aroma system 145 are small check valves 151 that prevent the back flow of scented air into the other fragrance pathways and keeps the fragrance cartridges 101 and fragrance infused substrates pure and discreet from fragrance contamination.

Figure 18:
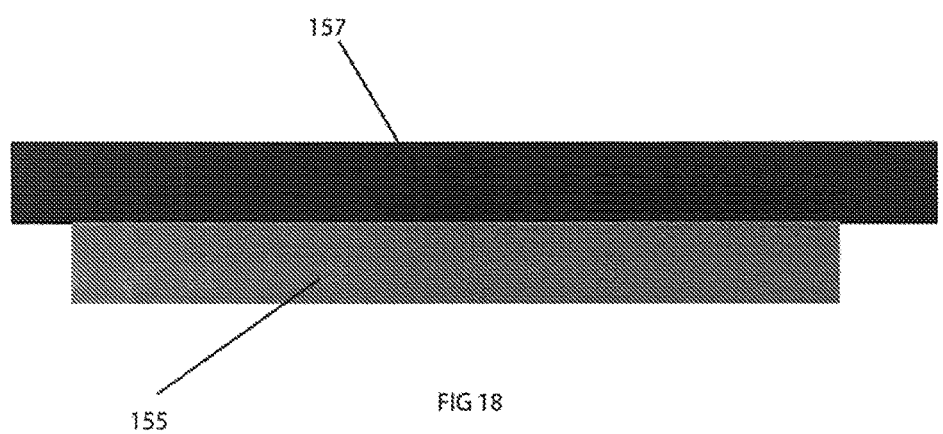
FIG. 18 illustrates a side view of a tablet computer with a digital aroma system attached to a back surface.
Figure 19:
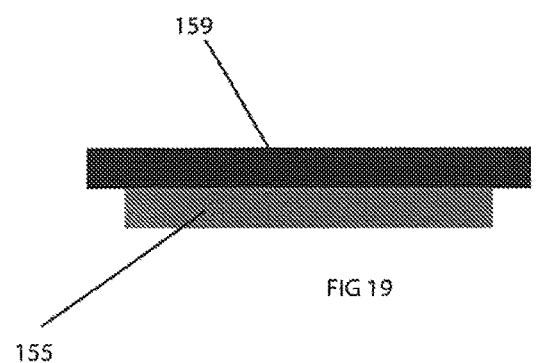
FIG. 19 illustrates a side view of a smart phone with a digital aroma system attached to a back surface.

In other embodiments, the digital fragrance system can be attached to various other portable computing devices such as tablet and smart phones. FIG. 18 illustrates a side view of a digital aroma system 155 attached to a back surface of a tablet computer 157 and FIG. 19 illustrates a side view of a digital aroma system 155 attached to a back surface of a tablet computer 157. The digital aroma system 155 can include interchangeable fragrance cartridges that are removably attached to a cassette and a manifold that can include fans or pumps and check valves. The digital aroma system 155 can be configured to direct scented air to an air outlet adjacent to the bottom edge of the tablet computer 157 or smart phone 159. However, tablet computers 157 and smart phones 159 can detect the orientation of the screen with accelerometers and adjust the displayed images so that they are always upright. In some embodiments, the digital aroma system 155 can adjust the air output to always be at emitting scented air from the bottom edge of the computing device regardless of the orientation of the digital aroma system 155. In an embodiment the digital aroma system 155 may include fans that normally pull the fresh air through the fragrance cartridges and out the bottom edge of the tablet computer 157. However, the digital aroma system 155 can also detect when the tablet computer 157 or smart phone 159 has been turned upside down. When this orientation change is detected, the fans can be controlled to operate in reverse the air flow to push fresh air from the new top through to the new bottom of the table computer 157.

Figure 20:
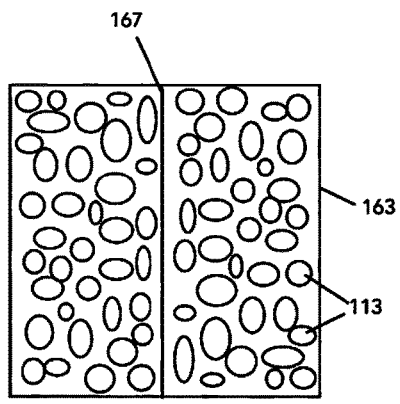
FIG. 20 illustrates top cross section view of an embodiment of a fragrance cartridge.
Figure 21:
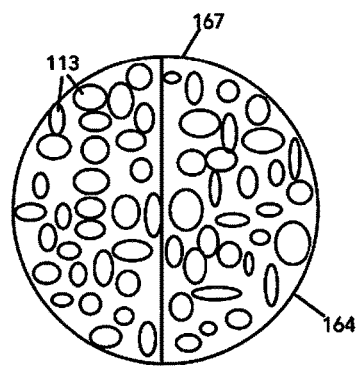
FIG. 21 illustrates side cross section view of an embodiment of a fragrance cartridge.

In different embodiments, the fragrance cartridges used with the digital aroma system can be configured with an air inlet and a scented air outlet on the same side of the fragrance cartridge. With reference to FIG. 20 is a top cross section view of a cube shaped housing 163 embodiment of a fragrance cartridge 162 which is at least partially filed with fragrance infused substrates. The fragrance cartridge 162 includes divider 167 that extends across a center the width of the housing 163. FIG. 21 illustrates a side cross section view of the cube shaped housing 163 embodiment of a fragrance cartridge 101 with a divider that is against the lower surface of the housing 163 but does not extend to the top of the housing 163. The arrows illustrating the flow path of air through air inlet holes in the bottom of the housing 163, over the divider and back through air outlet holes in the bottom of the housing 163.

Figure 22:
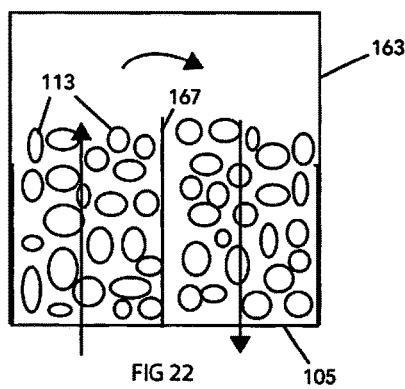
FIG. 22 illustrates top cross section view of an embodiment of a fragrance cartridge.
Figure 23:
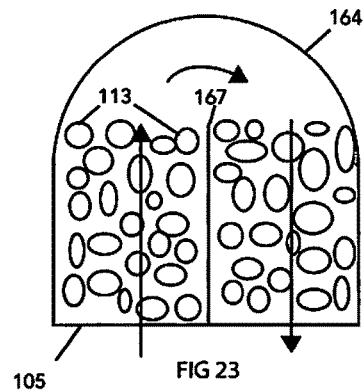
FIG. 23 illustrates side cross section view of an embodiment of a fragrance cartridge.

In other embodiments with reference to FIGS. 22 and 23, the fragrance cartridge 164 can have a bullet shaped housing with a lower cylindrical shaped housing and an upper half spherical shaped housing. The divider 167 is positioned against the lower surface of the housing 165 and provides a passageway above the divider 167. The arrows illustrating the flow path of air through air inlet holes in the bottom of the housing 164, over the divider and back through air outlet holes in the bottom of the housing 164.

Figure 24:
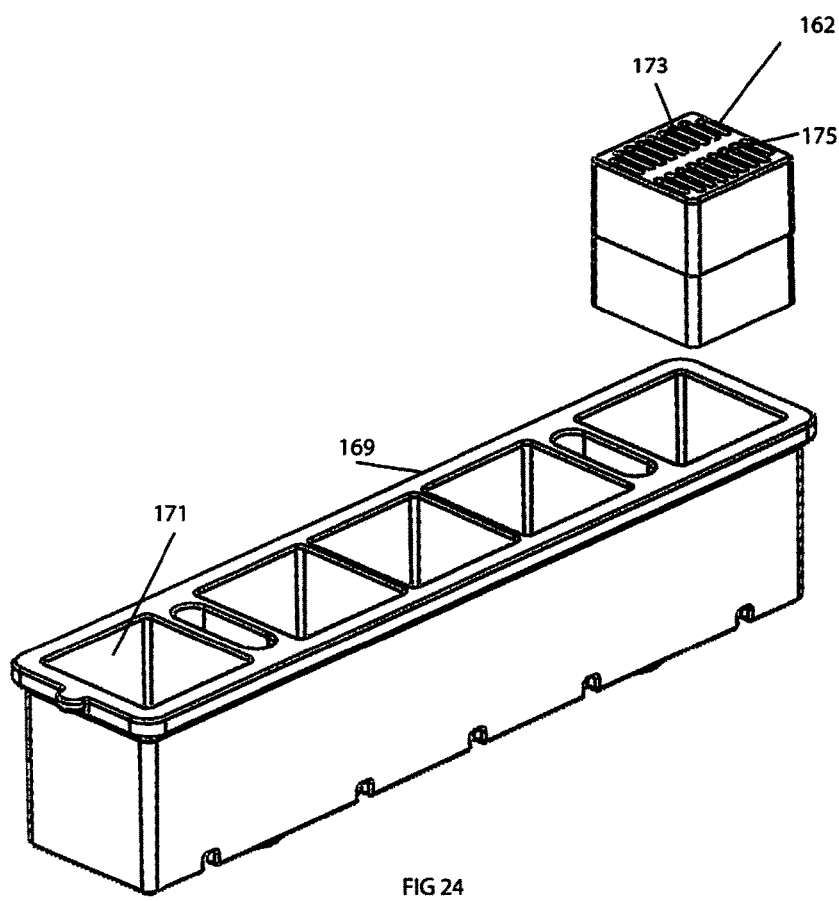
FIG. 24 illustrates a top perspective view of an embodiment of a fragrance cartridge cassette.

Because the cartridges have air inlets and scented air outlets on the same lower surface, the cartridges can be mounted in a cassette that holds the cartridges against a manifold that has both air inlets and scented air outlet paths. FIG. 24 illustrates a bottom perspective view of an embodiment of a cassette 169 that has open bottom slots 171 allow the individual fragrance cartridges 162. The fragrance cartridges 162 be inserted or replaced from the cassette 169. As discussed, the air inlet 173 and the scented air outlet 175 of the fragrance cartridge 162 can be on the same planar side surface of the cartridge 162. Thus, the top of the cartridge slot 171 can be closed since air does not flow through the cassette 169.

Figure 25:
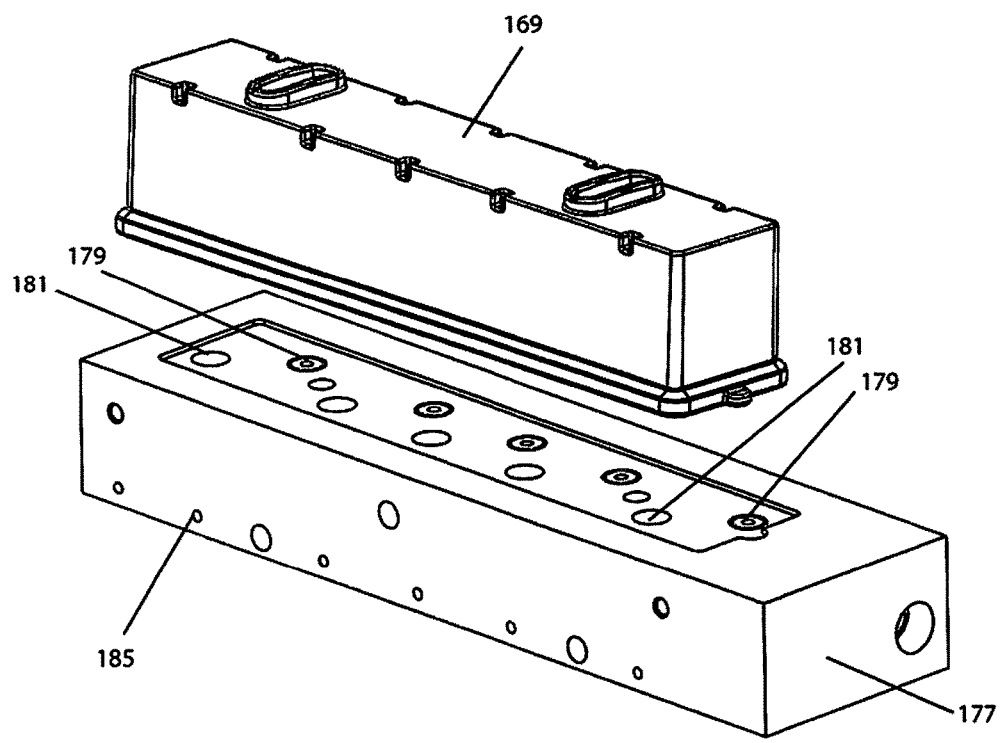
FIG. 25 illustrates a top perspective view of an embodiment of a cassette and a manifold module.

With reference to FIG. 25, a perspective view of an embodiment of the cassette 169 and a manifold module 177 is illustrated. The cassette 169 is in the upright position which shows the solid upper surface. The air inlet and scented air outlets of fragrance cartridges are exposed on the lower surface of the cassette 169. The manifold module 177 can have a recess 183 that corresponds with the outer perimeter of the cassette 169. The manifold module 177 can also have internal air passageways that are connected to the fragrance cartridges. In this embodiment, the manifold module has a row of fresh air outlet holes 179 and a row of scented air inlet holes 181. The cassette 169 can be placed in the recess 183 and held against the manifold module 177 with a releasable coupling mechanism. A gas seal such as an air tight gasket can be placed between the fragrance cartridges and the manifold module 177 to separate the different fragrance cartridges and seal the fresh air outlet holes 179 and air inlet holes 181. The side surfaces of the manifold module 177 can have side holes 185, which can be connected to the internal passageways within the manifold modules 177 and the fresh air outlet holes 179 and air inlet holes 181.

Figure 26:
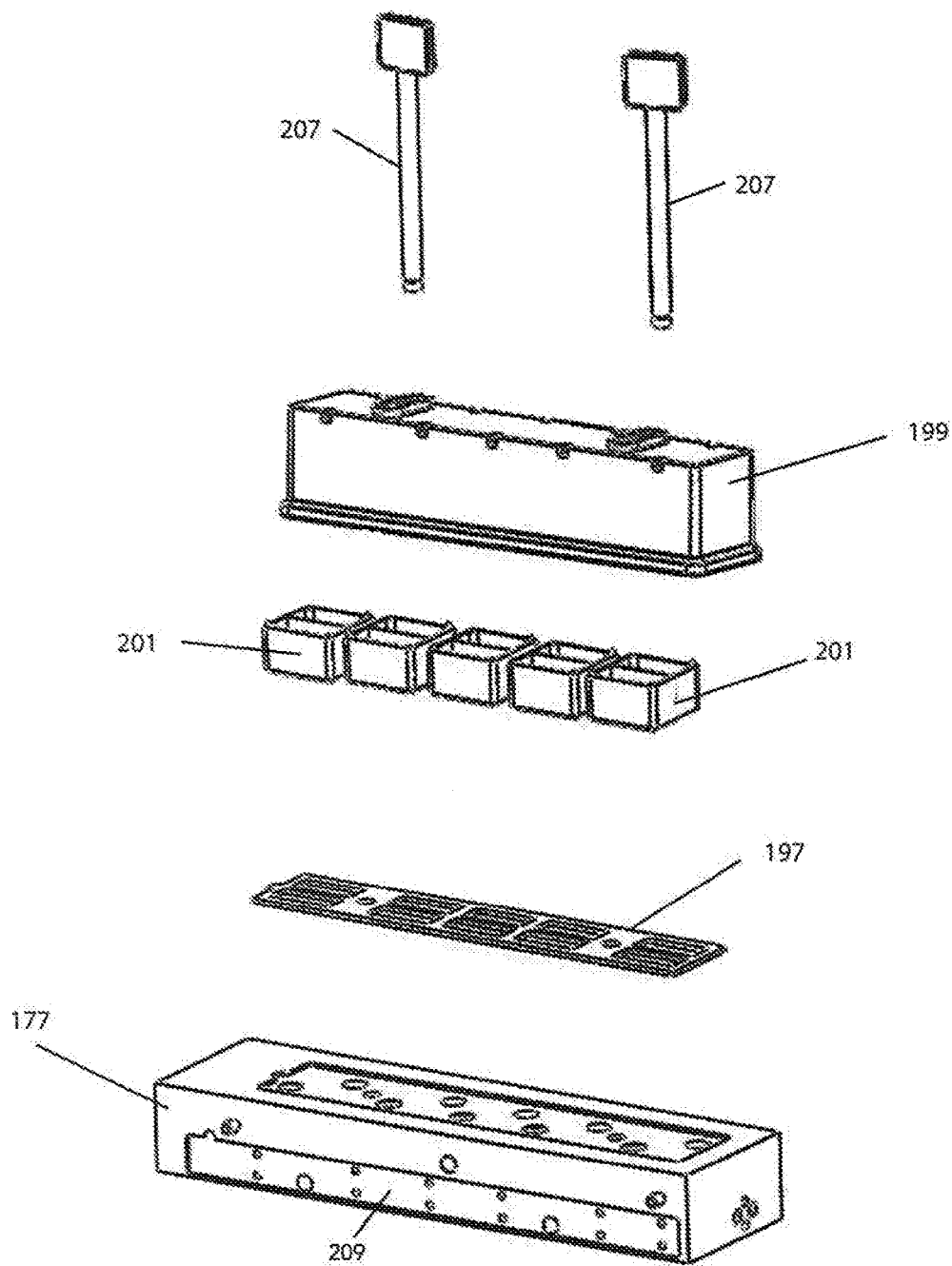
FIG. 26 illustrates a perspective exploded view of an embodiment of a cassette and a manifold module.

With reference to FIG. 26, an exploded view of a different embodiment of a manifold module 177 and cassette assembly is illustrated. In this embodiment, the assembly can include a cassette chamber 199 that surrounds a plurality of different cassette bead retainers 201 which can each have a different fragrance. Different fragrance infused substrates can be placed in each of the cassette bead retainers 201 that are within the cassette chamber 199. A cassette gasket seal 197 is placed between the cassette 169 and the manifold module 177 to prevent air from flowing between the different cassette bead retainers 201 or out the top and sides of the cassette chamber 199. The cassette assembly is held to the manifold module 177 by tightening locking pins 207 that extend through the cassette assembly components. The locking pins 207 can compresses the gasket 197 between the cassette chamber 199 and the manifold module 177 which creates an air tight assembly. When the adjacent manifold modules 177 are attached to each other, a manifold gasket 209 can be placed between the manifold modules 177 to create an air tight seals for the aligned and coupled side air holes.

Figure 27:
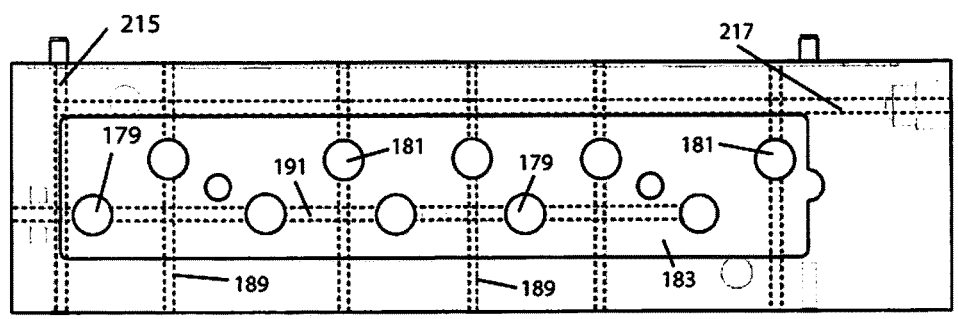
FIG. 27 illustrates a top view of an embodiment of a manifold module.

With reference to FIG. 27 a top view of an embodiment of a manifold module 177 which shows the internal passageways which include a length passageway 191 that is connected to the fresh air outlets 179 that extends along the length of the manifold module 177. The internal passageways also include parallel width passageways 189 that extend across the width of the manifold module 177 where each of the width passageways 189 are coupled to a scented air inlet 181. The length passageway 191 is offset vertically from the width passageways 189 so that they are not connected. The manifold module 177 can also include an inlet air passageway 215 that extends through the width of module 177 on one edge and an outlet scent passageway 217 that extends along the length of the module 177 on another edge. An inlet valves (not shown) can be coupled to the length passageway 191 and outlet valves can be coupled to the width passageways. When actuated to open the inlet valve can connect the length passageway 191 to the inlet air passageway 215 and the outlet valves can connect the width passageways to the outlet scent passageway 217. When multiple modules 177 are connected, the inlet air passageways 215 can be connected to form a longer inlet air passageway that extends across the entire width of the assembly. In contrast, when multiple modules 177 are connected, the system may only use the outlet scent passageway 217 of the end module 177 with the outlet scent passageways 217 of the other modules 177 being unused.

Figure 28:
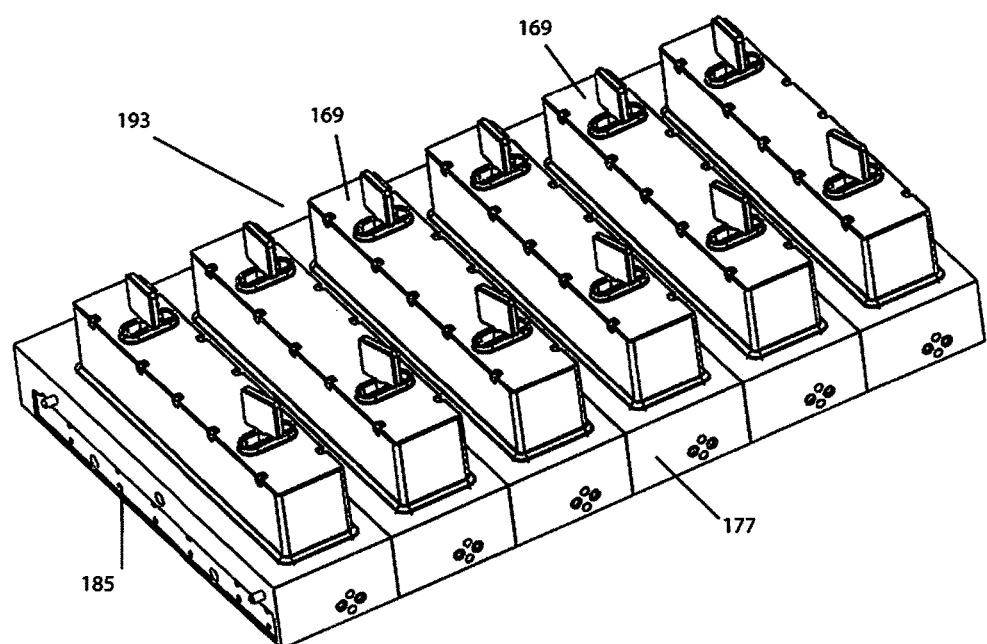
FIG. 28 illustrates a top perspective view of an embodiment of a manifold assembly with cassettes.
Figure 29:
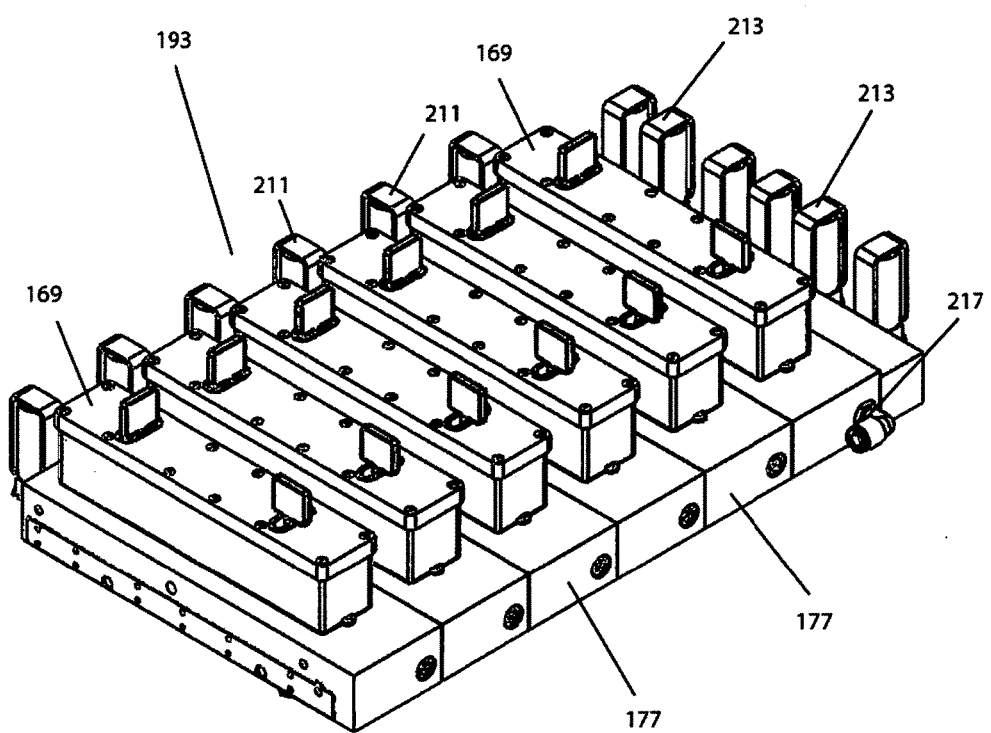
FIG. 29 illustrates a top perspective view of an embodiment of a digital aroma system.

With reference to FIG. 28, multiple manifold modules 177 can be coupled together with the side holes 185 aligned to form a larger digital fragrance system. By connecting and sealing the side holes 185 to the side holes 185 of the adjacent manifold module 177, the digital fragrance system can be expanded to include any number of fragrance cartridges. In the illustrated example, there are six manifold modules 177 with each of the manifold modules 177 containing five fragrance cartridges. In this example, the illustrated digital aroma system assembly 193 can include a total of thirty fragrance cartridges. With reference to FIG. 29, a plurality of inlet valves 211 can be coupled to the inlet air passageways on one end of each of the manifold modules 177. A plurality of outlet valves 213 can be coupled to the outlet scent passageways on one of the end manifold modules 177 and the opposite ends of the outlet scent passageways can be sealed to prevent air from escaping. Air can be directed through the digital fragrance system to any individual fragrance cartridge by controlling the open/closed positions of the inlet valves 211 and the outlet valves 213.

Figure 30:
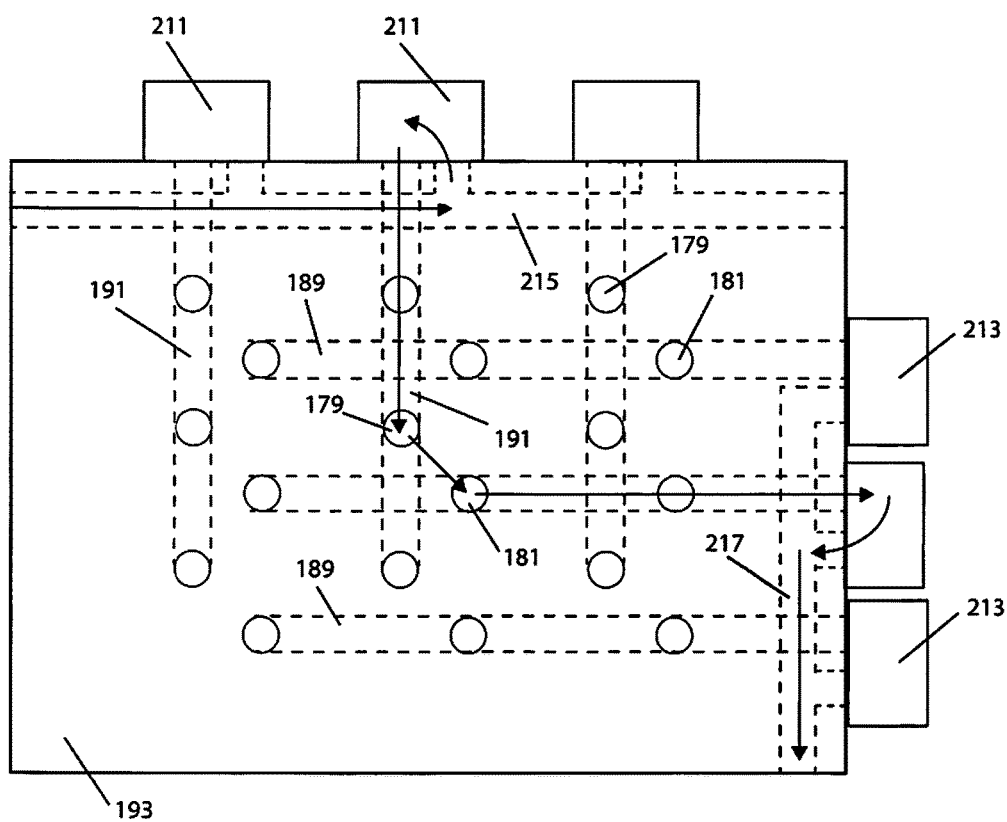
FIG. 30 illustrates a top view of air flow through an embodiment of a digital aroma system.

With reference to FIG. 30, the digital aroma system 193 formed from a plurality of manifold modules can have an array of internal passageways 161 which can be coupled to inlet valves 211 and outlet valves 213 which are opened and closed to control the scented air outlet path. By actuating (opening) one inlet valve 211 and one outlet valve 213 and keeping all other inlet valves 211 and outlet valves 213 closed, a passageway to a specific fragrance cartridge can be selected by the digital aroma system. FIG. 30 illustrates a top view of a simplified embodiment of a digital aroma system 193 configured with nine fragrance cartridges spaces for clarity. Each cartridge space includes a fresh air inlet 179 and a scented air outlet 181. In an embodiment pressurized air from a fan or pump can be applied to the inlet air passageway 215. When one of the inlet valves 211 is actuated pressurized air can flow through the corresponding length passageway on a selected row of fragrance cartridges on a single cassette. When one of the outlet valves 213 is open, air can flow through the fragrance cartridges and scented air can flow to the outlet passageway 217. From the simplified digital aroma system 193, the scented air can be directed towards the nose of the system user. In an alternative embodiment a vacuum or low pressure from a fan or pump can be applied to the outlet scent passageway 217. When one of the inlet valves 211 air can pulled through the corresponding length passageway on a manifold module 177. Air can then flow through one of the fragrance cartridges to the outlet passageway 217 through the fan or pump and be directed towards the nose of the system user. The valves can be actuated by a valve controller(s) that is controlled by a system processor in response to a scent release signal or trigger. Each individual fragrance stored in the digital aroma system 193 can be output by actuating a combination of one inlet valve and one outlet valve. In some embodiments, it can be desirable to mix a plurality of fragrances which can be performed by opening valves to a plurality of fragrance cartridges.

Figure 31:
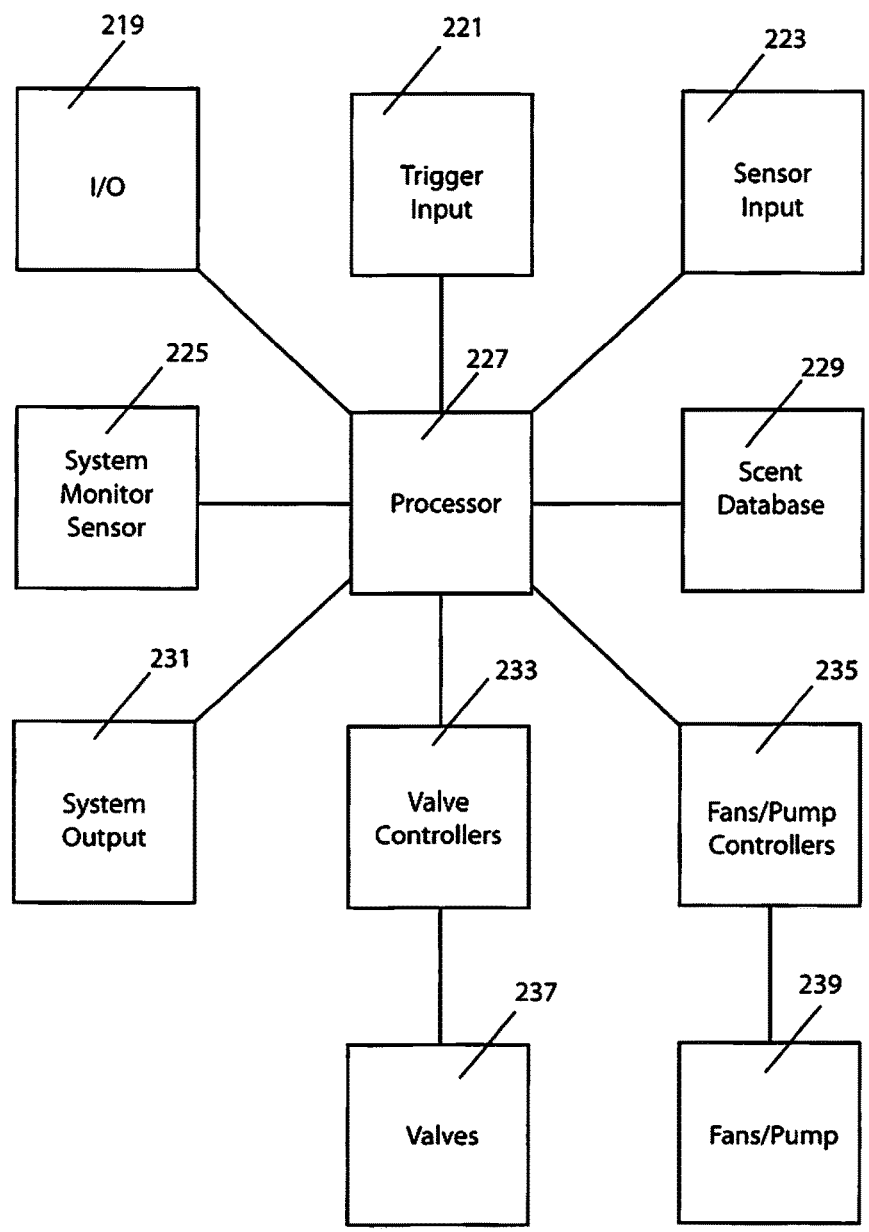
FIG. 31 illustrates a block diagram of components for an embodiment of a digital aroma system.

FIG. 31 illustrates a block diagram of possible components of a digital aroma system which can include: an I/O 219, a trigger input 221, a sensor input 223, system monitor sensors 225, processor 227, a scent database 229, a system monitor sensor 225, a processor 227, a scent database 229, a system output 231, valve controllers 233, vales 237, fan/pump controllers 239 and fans/pumps 239. The I/O 219 can be a transceiver that allows communications between the digital aroma system and other media devices, servers, smartphones, servers, other digital aroma system and other computing devices. In an embodiment, the I/O 219 can provide system communications wirelessly through Blue Tooth, Wi-Fi, RFID or similar technologies with other devices which can provide control signals for releasing fragrances. The trigger input 221 is an input for control signals from devices such as media players, video games, etc. In an embodiment, the trigger input 221 can provide system communications wirelessly through Blue Tooth, Wi-Fi, RFID or similar technologies with other devices which can provide control signals for releasing fragrances.

When the digital aroma system is used, it can go through a startup procedure which identifies each fragrance cartridge stored in the system. As discussed, the fragrance cartridges can have an identification system, which are read by the system monitor sensors 225. For example, in an embodiment each of the plurality of fragrance cartridges includes an RFID tag that identifies a scent of the dry fragrance cartridge and an RFID reader reads the RFID tags of the fragrance cartridges. The RFID readers can be system monitor sensors 225. The digital aroma system includes a visual display which can be a system output 231 for displaying the scent of the dry fragrance cartridge. The system can then match the different fragrance cartridges to the various fragrance triggers and store this information in the scent database 229. The system can emit the target fragrance when the corresponding trigger is detected by the trigger input 221 or other signals are detected by one of the sensor inputs 223.

The sensor input 223 can be a sensor that detects ambient signals such as a microphone that detects audio signal or a camera that can detect a video image. The system monitor sensor 225 can be coupled to the digital aroma system components and detect the operation of the components. The scent database 229 can include a list of fragrances information which can be used to match the fragrance based upon a fragrance identification code signal and then the identification with the valves 237 that must be open to actuate the release of the identified fragrance. The system output 231 can be a visual output, which can be used to inform the system user of system errors or cartridge replacement needs. The valve controllers 233 allow the processor 227 to control the operation of the valves 237. The fans/pumps controllers 235 can be used to allow the processor 227 to control the operation of the fans/pumps. The described digital aroma system components can operate in conjunction to perform various functional actions that can be performed with software running on the processor 227.

In some embodiments, the digital aroma system can recognize video encoded fragrance markers in the video media. The encoded fragrance markers can identify a specific fragrance that is read by the video object recognition system resulting in the identified fragrance being delivered to the user. This feature can be useful in providing a smell before an image corresponding to the fragrance is displayed. For example, the camera point of view in a video may be approaching a fire. The smoke from the fire may be blowing towards the camera and a person at the camera position may smell the smoke before seeing the fire. In order to accurately recreate this scenario the video media may use an encoded fragrance marker for smoke, which is detected by the video object recognition system. The video object recognition system can then emit the smoke fragrance before the fire is shown on the video.

For example, a digital media can include aroma output signals which can be a video encoded fragrance marker and the media player can transmit the scent output signal(s) to the trigger input 221 which can be received by the processor 227. The aroma output signals can include an aroma identification and the processor 227 can access the scent database 229 to identify the location of the corresponding fragrance cartridge and the valves that must be open to access the identified fragrance cartridge. The processor 227 can then transmit control signals to the valve controllers 233 which actuate the valves 237 to open an airflow path to the identified fragrance cartridge.

In an embodiment the trigger input can be transmitted within a short range proximity through a device such as a Bluetooth receiver or other local communications device. The aroma system can be used with a mobile device such as a smart phone that is carried by the user. When the user walks within a museum to different exhibits, the trigger input 221 of the digital aroma system can detect trigger signals from different exhibits as the user walks and the aroma system can emit the scent as commanded by the detected trigger signals. In other embodiments, the present invention can be used in many different individual educational settings like museums to provide a cost effective sensory experience using media, software, maintenance and aroma.

In an embodiment, the digital aroma system can emit fragrances in response to a digital fragrance control signal from a video game. The digital aroma system may communicates with a computing device that is running video game software through the trigger input 221. The video game software can include one or more lines of code that identifies a fragrance and causes a trigger signal for the fragrance to be transmitted to the trigger input at the correct time during game play. The video game software can be local software running in the remote device, remote software running on a remote computing device such as a video game console and/or remote online software stored or running in a cloud based computing network system.

In an embodiment, the sensor input 223 can be a camera and the processor 227 can run a video object recognition software that receive video signals from the sensor input 223 camera and recognize objects and/or environments before these video images are displayed on a video output display. In an embodiment there maybe a known time delay between the actuation of the digital aroma system to output a target fragrance and the user smelling the fragrance. The video object recognition system can identify the fragrance video object and/or environment trigger and identify the fragrance that is associated with the trigger. The digital aroma system can then actuate the trigger associated fragrance delivery before the trigger object or environment is displayed by the known time delay period so that the fragrance is delivered to the viewer at the moment when the trigger object or environment is being displayed.

In an embodiment the digital aroma system can use a microphone as a sensor input 223 that can be triggered the correct aroma with sound recognition software running on the processor 227 that recognizes the sounds in the game or movie and disperses the correct aroma based on sound. The audio recognition system can receive the audio signals and use the scent database 229 to identify the fragrance associated with the audio signals. The processor 227 running audio recognition software can then control the valves 237 and fans/pumps 239 to actuate the fragrance delivery.

The digital aroma system can couple the trigger input 221 to a media player to detect audio signals for playback in an audio or video media before the corresponding audio or video are output by the media player to the user. For example, a video media being played may include fireworks and the distinctive sounds of the firework explosions. The audio trigger recognition software running on the processor 227 may identify the fireworks sound and associate this sound with the fragrance of burning sulfur. In an embodiment, the audio recognition system may detect the fragrance associated audio signal through the scent database 229 and the audio recognition software on the processor 227 may actuate the delivery of the fragrance by actuating the correct set of valves 237 before the audio trigger is output through the speaker by the known time delay period so that the fragrance is delivered to the viewer at the moment when the audio trigger sound is being heard.

In another embodiment, the sensor input 223 can be a microphone can receive audio signals and the processor 227 can identify the audio signals and cause the valves 237 to output a fragrance that corresponds to the identified audio signals. For example, if an explosive audio signal is detected, the processor 227 can match the explosive audio signal with a burning smell and control the valves 237 to release this aroma.

In another embodiment the trigger input 221 can receive video image data before it is displayed by the media player. For example, an image of flowers can be received by a trigger input 221 of the digital aroma system. The processor 227 running image identification software can identify the flower image and the system can be programmed to emit a floral fragrance by actuating the proper set of valves 237 in response to the image identification software detecting an image of flowers.

In other embodiments, the digital aroma system can be configured to emit a specific fragrance in response to identified video images with a sensor input 223 which can be a camera. For example, the image software can be configured to associate specific detected images with specific fragrances. A beach image which can be part of a video game or a video playback can result in the system emitting a corresponding beach fragrance. When a beach image is detected by the camera sensor input 223, the processor 227 can control the valves 237 to emit a beach fragrance. In other embodiments, various other images can result in corresponding fragrances, for example, a lawn image can have a corresponding grass fragrance, a Thanksgiving dinner image can have a roasted turkey fragrance, etc. When the grass image is detected the processor 227 can cause the valves 237 to emit a grass scent and when a Thanksgiving dinner is detected the processor 227 can emit a roasted turkey smell.

In an embodiment, the digital aroma system can include software running on the local processor that can communicate through the I/O 219 to the Internet to a cloud service. This communication capability can be used with the system monitor sensor 225 for remote monitoring of the cassettes and fragrance cartridges, the duration of the number of uses, and remotely monitors the health of the pump and/or fan and health in the digital aroma system to ensure the system components are working properly. If errors or end of life are detected in any of the system components, the processor 227 of the digital aroma system sends alerts to a user or system administrator identifying the errors through the system output 231 when something is not working properly. The system output 231 can be a visual display, an audio output device and/or a digital wireless communication output.

The present invention addresses several issues that are currently found in gaming and movie environments. Some fragrance systems have been tried to use scented oils, which are cumbersome and messy. In contrast, the inventive digital aroma system uses fragrance cartridges which have dry beaded sealed units coupled to a cassette and manifold which provides a self-contained system. The fragrance is from dry particles which are infused into substrates such as beads that remain enclosed in individual chambers that seals the aroma for freshness until the fragrance cartridge is installed in the digital aroma system and delivered through the scent outlet to the user. Because of the dry nature of the fragrance materials there is no lingering aroma effect and no volatile organic compounds (VOCs).

In the present digital aroma system invention, the user can easily change the fragrance cartridges and may only need to replace the cartridges every few months depending upon the scent use. In an embodiment, the digital aroma system can monitor the number of times each of the fragrance cartridges is used. When the life of the cartridge is reaching its end, the system can warn the user that the cartridge needs to be replaced. Thus, the cartridge only that needs to be replaced as needed. The longevity of each dry fragrance infused beaded cartridge is anywhere from 1,000-4,500 dispersions. In other embodiments, fragrance cartridges with larger chambers that holds more fragrance infused substrate materials can last longer with more dispersions.

The present digital aroma system invention also addresses the issue of ease of replacement of the fragrance cartridges by the consumer. The digital aroma system allows the swapping out of several fragrances simultaneously by removing and replacing a single cassette of the digital aroma system. The cassette can contain six or more individual fragrance cartridges containing dry fragrance infused substrate materials. In other embodiments, the cassette is not limited to six fragrance cartridges. For example, the cassette can hold a single fragrance cartridge and in other embodiments the cassette can have couplings to hold ten to twenty or more fragrance cartridges and in a cassette system. In addition the consumer can also change each individual aroma cartridge within the cassette system be simply exchanging each aroma cartridge within the cassette or replacing the entire cassette.

The digital aroma system invention may allow a gaming media team to change out a digital representation of the aroma completely with a simple content media change either locally or remotely. For example, the digital aroma system may have eight fragrance cartridges that are divided into two sets of four fragrances. The digital representation of the sets of fragrances can be change remotely or locally so that the sets of fragrances can be easily changed. This changing of fragrance sets can provide additional to the functionality of the digital aroma system. For example, in an embodiment the digital aroma system may have multiple fragrance intensity settings. In an embodiment, the digital aroma system can be configured to allow a user to change the intensity between high fragrance intensity and low fragrance intensity.

The digital aroma system can include a cassette having a manifold, which holds a plurality of fragrance cartridges. The manifold has air inlets and scent outlets that are coupled to the fragrance cartridges which can have hollow housings which are filled with dry fragrance infused particles such as balls or other loose objects. The cartridge housings can have couplings such as threads or tabs, which can provide a gas tight connection between the cartridges and the manifold. The couplings also allow users to replace or change the fragrance cartridges. The cartridges can also have identification mechanisms which provide an identification signal output such as a radio frequency identification tag. The identification signal output can identify the fragrance in the cartridge and control the number of fragrance outputs that the cartridge can provide. The digital aroma system can have readers, which can read the identities of the fragrance in the cartridges and store this fragrance and cartridge location information so that desired fragrance can be controlled to emit by the digital aroma system.

For the sake of clarity, the processes and methods herein have been illustrated with a specific flow, but it should be understood that other sequences may be possible and that some may be performed in parallel, without departing from the spirit of the invention. Additionally, steps may be subdivided or combined. As disclosed herein, software written in accordance with the present invention may be stored in some form of computer-readable medium, such as memory or CD-ROM, or transmitted over a network, and executed by a processor.

All references cited herein are intended to be incorporated by reference. Although the present invention has been described above in terms of specific embodiments, it is anticipated that alterations and modifications to this invention will no doubt become apparent to those skilled in the art and may be practiced within the scope and equivalents of the appended claims. More than one computer may be used, such as by using multiple computers in a parallel or load-sharing arrangement or distributing tasks across multiple computers such that, as a whole, they perform the functions of the components identified herein; i.e. they take the place of a single computer. Various functions described above may be performed by a single process or groups of processes, on a single computer or distributed over several computers. Processes may invoke other processes to handle certain tasks. A single storage device may be used, or several may be used to take the place of a single storage device. The present embodiments are to be considered as illustrative and not restrictive, and the invention is not to be limited to the details given herein. It is therefore intended that the disclosure and following claims be interpreted as covering all such alterations and modifications as fall within the true spirit and scope of the invention.

What is claimed is:
1. A digital aroma system comprising:
  a plurality of fragrance cartridges, each of the fragrance cartridges comprising:
    a cartridge housing; and
    a plurality of dry fragrance infused substrates within the cartridge housing;
  a cassette for holding the plurality of fragrance cartridges, the cassette having a manifold with air passages wherein each of the plurality of fragrance cartridges are individually removable from the cassette wherein each of the air passages has an air inlet and a scent outlet;
  a pump or a fan directing air through the air inlet in the manifold and transmitting some of the dry fragrance from one of the plurality of fragrance cartridges to the scent outlet; and
  a receiver for receiving digital aroma signals coupled to a processor that selectively controls a plurality of control valves that transmit the dry fragrances from the plurality of fragrance cartridges to the scent outlet.

2. The digital aroma system of claim 1, wherein the digital aroma signals are transmitted from at least one of: a video game, a television, and a video player playing a movie.

3. The digital aroma system of claim 1, wherein the air inlets and air outlets of the manifold form a matrix and the dry fragrance infused substrates are beads or substrate materials infused with a plurality of different fragrances.

4. The digital aroma system of claim 1, wherein each of the plurality of fragrance cartridges includes a coupling mechanism, and each of the plurality of fragrance cartridges are interchangeable on the cassette.

5. The digital aroma system of claim 1, wherein each of the plurality of fragrance cartridges includes a radio frequency identification (RFID) tag that identifies a scent of the dry fragrance cartridge, the processor is coupled to an RFID reader which reads the RFID tags of the fragrance cartridges and the digital aroma system includes a visual display for displaying the scent of the dry fragrance cartridge.

6. The digital aroma system of claim 1, wherein an airflow output of the fan or the pump is controlled by the processor.

7. The digital aroma system of claim 1, further comprising:
a plurality of fans, wherein each of the plurality of fans is one of the air passages and controlled by the processor to an off setting or an on setting so that air is directed through one of the plurality of fragrance cartridges.

8. The digital aroma system of claim 1, further comprising:
an outlet nozzle coupled to the scent outlet, wherein the dry fragrance from one of the plurality of fragrance cartridges to the outlet nozzle.

9. The digital aroma system of claim 1, wherein the processor is in communication with a media player playing digital media on a visual display and the transmission of the dry fragrances from the scent outlet is triggered by events in the digital media.

10. The digital aroma system of claim 9, wherein media is a video game or video media.

11. The digital aroma system of claim 9, wherein the transmission of the dry fragrance is triggered by a visual event in the digital media, wherein the visual event is the display of a place or an object on the visual display that is recognized by the digital aroma system and the dry fragrance transmitted by the digital aroma system corresponds to the visual event.

12. The digital aroma system of claim 9, wherein the transmission of the dry fragrance is triggered by an audio event in the digital media, wherein the audio event is an audio output of a sound that is recognized by the digital aroma system and the dry fragrance transmitted by the digital aroma system corresponds to the audio event.

13. The digital aroma system of claim 9, further comprising:
an audio sensor for detecting spoken instructions, wherein the dry fragrance transmitted to the scent outlet matches to the spoken instructions.

14. The digital aroma system of claim 1, further comprising:
a plurality of pressure sensors coupled to the processor, wherein when air flows through the fragrance cartridges a pressure differential across the fragrance cartridges is measured by the pressure sensors and the processor emits a valve error signal when the pressure differential across is above a predetermined expected pressure differential range.

15. The digital aroma system of claim 1, further comprising:
a plurality of pressure sensors coupled to the processor, wherein when air flows through the fragrance cartridges a pressure differential across the fragrance cartridges is measured by the pressure sensors and the processor emits a fan error signal when the pressure differential across is below a predetermined expected pressure differential range.

16. The digital aroma system of claim 1, wherein the processor is coupled to an input for receiving a program for the transmission of the dry fragrance from a remote computing device.

17. The digital aroma system of claim 1, wherein the plurality of fragrance cartridges, each comprise a partition mounted within the housing which causes air to flow though the plurality of dry fragrance infused structures within the cartridge housing.

18. The digital aroma system of claim 1, wherein the cassette chamber has a separate capsule grid that keeps the solid fragrance material from blocking the chamber passage way.

19. The digital aroma system of claim 1, wherein the manifold is expandable by connecting an additional manifold to create a system that can accommodate additional fragrance cartridges.

20. The digital aroma system of claim 1, wherein each scent output in the manifold has a one way check valve which prevents the dry fragrance from flowing through the air inlet.

21. The digital aroma system of claim 1, wherein the fan or the pump pushes the air through the manifold to cause the dry fragrances from the plurality of fragrance cartridges to flow through the scent outlet.

22. The digital aroma system of claim 1, wherein the fan or the pump pulls the air through the manifold to cause the dry fragrances from the plurality of fragrance cartridges to flow through the scent outlet.

23. The digital aroma system of claim 1, wherein the processor controls the opening and closing of valves to cause air flow through the air input and scent output passageway in the manifold, the cassette and the fragrance cartridge to provide a selected fragrance.

24. The digital aroma system of claim 1, wherein programmable software is running on the processor to control the flow of air through the manifold, the cassette and the fragrance cartridge to provide a selected fragrance.

25. The digital aroma system of claim 1, wherein the processor is programed with interactive media software.

26. The digital aroma system of claim 1, wherein the cassette can hold one cartridge or many cartridges at least partially filled with the dry fragrance infused structures.

27. The digital aroma system of claim 1, wherein the processor runs software that controls the digital aroma system.

28. The digital aroma system of claim 1, wherein computer software running on the processor creates a visual output, an audio output, and a smell output.

29. The digital aroma system of claim 1, wherein the manifold includes a solenoid that is opened to direct clean air through the manifold to purge the fragrance from the manifold after a dispersion of the dry fragrances from the plurality of fragrance cartridges to the scent outlet.

30. The digital aroma system of claim 1, wherein the processor is computer controlled and computer monitored using both a local computer and a cloud based server and software.

31. The digital aroma system of claim 1, wherein the processor is programmed using communication connections, servers and software.

32. The digital aroma system of claim 1, wherein the processor can be connected to a communications network and to a cloud service for remote monitoring that shows changing of the dry fragrances transmitted from the plurality of fragrance cartridges to the scent outlet.

33. The digital aroma system of claim 1, wherein the processor is connected through communications network to a computer to monitor each the plurality of fragrance cartridges and determine replacement cycles of the fragrance cartridges.

34. The digital aroma system of claim 1, wherein the processor can be programmed to change the duration of time that the air flow passes through the plurality of fragrance cartridges to the scent outlet.

35. The digital aroma system of claim 1, wherein the processor can be connected through communications network to remotely monitor the health of the fan or the pump.

36. The digital aroma system of claim 1, wherein each scent output in the manifold has a one way check valve which prevents the dry fragrance from flowing through the air inlet and the processor can be connected through communications network to remotely monitor the health of the one way check valve in the system to ensure proper function and operation.

37. The digital aroma system of claim 1, wherein a computer can reside in the cloud and a remote server application running on the computer can interact with the processor and providing live interactive experiences.

38. The digital aroma system of claim 1, wherein the processor can be programmed to mix two or more of the dry fragrances and deliver the two or more of the dry fragrances to the scent outlet.

39. The digital aroma system of claim 1, wherein the plurality of the fragrance cartridges are coupled to the cassette and the cassette with the plurality of the fragrance cartridges is removable from the digital aroma system.

40. The digital aroma system of claim 1, wherein the cassette simultaneously holds 1 to 20 fragrance cartridges.

41. The digital aroma system of claim 1, wherein clean air is transmitted through the manifold for a predetermined period of time after each transmission of the dry fragrances from the plurality of fragrance cartridges to the scent outlet.

42. The digital aroma system of claim 1, wherein a media team changes out a digital representation of the fragrance cartridges with a content media change.

43. The digital aroma system of claim 1, further comprising a pressure sensor coupled to the processor wherein each scent output in the manifold has a one way check valve which prevents the dry fragrance from flowing through the air inlet and the processor monitors a pressure of the digital aroma system and transmits pressure information via a communications link to a server to determine that the fan or the pump and the one way check valve are working.

44. The digital aroma system of claim 43, wherein cloud based software and a server system are notified via the processor of failures of the one way check valve or the fan or the pump.

* * * * *